US006025332A

United States Patent [19]
Mascarenhas

[11] Patent Number: 6,025,332
[45] Date of Patent: *Feb. 15, 2000

[54] METHOD FOR TREATING LOW CIRCULATING LEVELS OF SEX HORMONE STEROIDS ASSOCIATED WITH AGING USING IGF OR IGF/IGFBP-3

[75] Inventor: Desmond Mascarenhas, Los Altos Hills, Calif.

[73] Assignee: Celtrix Pharmaceuticals, Inc., San Jose, Calif.

[*] Notice: This patent is subject to a terminal disclaimer.

[21] Appl. No.: 09/088,618

[22] Filed: Jun. 1, 1998

Related U.S. Application Data

[63] Continuation-in-part of application No. 08/837,603, Apr. 21, 1997, which is a continuation-in-part of application No. 08/805,807, Feb. 25, 1997.

[51] Int. Cl.⁷ .................................................. A61K 38/25
[52] U.S. Cl. ................................ 514/12; 514/3; 514/866; 424/198.1; 424/546; 552/502
[58] Field of Search .................. 514/12, 3, 866; 424/198.1, 546; 552/502

[56] References Cited

U.S. PATENT DOCUMENTS

| | | | |
|---|---|---|---|
| 4,835,147 | 5/1989 | Roberts | 514/178 |
| 4,988,675 | 1/1991 | Froesch et al. | 514/12 |
| 5,068,224 | 11/1991 | Fryklund et al. | 514/12 |
| 5,077,284 | 12/1991 | Loria et al. | 514/171 |
| 5,093,317 | 3/1992 | Lewis et al. | 514/12 |
| 5,106,832 | 4/1992 | Froesch et al. | 514/12 |
| 5,128,320 | 7/1992 | Hahn et al. | 514/12 |
| 5,162,198 | 11/1992 | Eich et al. | 514/12 |
| 5,187,151 | 2/1993 | Clark et al. | 514/3 |
| 5,200,509 | 4/1993 | Spencer et al. | 530/350 |
| 5,202,119 | 4/1993 | Clark et al. | 424/88 |
| 5,273,961 | 12/1993 | Clark | 514/8 |
| 5,407,684 | 4/1995 | Loria et al. | 424/442 |
| 5,407,913 | 4/1995 | Sommer et al. | 514/12 |
| 5,407,927 | 4/1995 | Morales et al. | 514/177 |
| 5,420,112 | 5/1995 | Lewis et al. | 514/12 |
| 5,434,134 | 7/1995 | Gluckman et al. | 514/12 |
| 5,527,776 | 6/1996 | Carlino et al. | 514/12 |
| 5,527,789 | 6/1996 | Nyce | 514/178 |
| 5,534,493 | 7/1996 | Gluckman et al. | 514/12 |
| 5,637,567 | 6/1997 | Moses et al. | 514/12 |
| 5,736,515 | 4/1998 | Bengtsson et al. | 514/12 |

FOREIGN PATENT DOCUMENTS

| | | |
|---|---|---|
| 0 128 733 | 12/1984 | European Pat. Off. . |
| 0 560 723 | 9/1993 | European Pat. Off. . |
| 0 436 469 | 2/1995 | European Pat. Off. . |
| 0 434 625 | 4/1995 | European Pat. Off. . |
| WO 91/12018 | 8/1991 | WIPO . |
| WO 92/00754 | 1/1992 | WIPO . |
| WO 93/02695 | 2/1993 | WIPO . |
| WO 93/08826 | 5/1993 | WIPO . |
| WO 93/23071 | 11/1993 | WIPO . |
| WO 94/16709 | 8/1994 | WIPO . |
| WO 95/03817 | 2/1995 | WIPO . |
| WO 95/04076 | 2/1995 | WIPO . |
| WO 95/08567 | 3/1995 | WIPO . |
| WO 95/13823 | 5/1995 | WIPO . |
| WO 95/13824 | 5/1995 | WIPO . |
| WO 96/02565 | 2/1996 | WIPO . |
| WO 96/40736 | 12/1996 | WIPO . |

OTHER PUBLICATIONS

Aberg et al., "Increases in tissue levels of ubiquionone in association with peroxisome proliferation" *Chem. Biol. Inter.* (1996) 99:205–218.

Almenoff et al., "Bronchodilatory effects of ipratropium bromide in patients with tetraplegia" *Paraplegia* (1995) 33:274–277.

Almenoff et al., "Pulmonary function survey in spinal cord injury: Influences of smoking and level and completeness of injury" *Lung* (1995) 173:297–306.

Andrews et al., "Contemporary management of depression" *Am. J. Med.* (1994) 97:6A–24S–6A–32S.

Baker et al., "Effects of an Igfl gene null mutation on mouse reproduction" *Mol. Endocrinol.* (1996) 10:903–918.

Bauman et al., "Blunted growth hormone response to intravenous arginine in subjects with a spinal cord injury" *Horm. Metab. Res.* (1994) 26:152–156.

Bauman et al., "Chronic baclofen therapy improves the blunted growth hormone response to intravenous arginine in subjects with spinal cord injury" *J. Clin. Endocrinol. Metab.* (1994) 78:1135–1138.

Bauman et al., "Disorders of carbohydrate and lipid metabolism in veterans with paraplegia or quadriplegia: A model of premature aging" *Metabolism* (1994) 43:749–756.

Baxter et al., "Growth hormone–dependent insulin–like growth factor (IGF) binding protein from human plasma differs from other human IGF binding proteins" *Biochem. Biophys. Res. Comm.* (1986) 139:1256–1261.

Baxter et al., "Structural determinants for binary and ternary complex formation between insulin–like growth factor–I (IGF–I) and IGF binding protein–3" *J. Biol. Chem.* (1992) 267:60–65.

(List continued on next page.)

*Primary Examiner*—F. T. Moezie
*Attorney, Agent, or Firm*—Morrison&Foerster LLP

[57] ABSTRACT

Methods are provided for treating or alleviating the symptoms of subjects with psychological disorders, metabolic disorders, chronic stress-related disorders, sleep disorders, conditions associated with sexual senescence, aging, or premature aging by treating such subjects with IGF or mutant IGF either alone or complexed with IGFBP-3. Methods for increasing the levels of DHEA or DHEAS and treating or alleviating the symptoms of subjects with disorders characterized by low levels of DHEA or DHEAS by administering effective amounts of IGF or mutant IGF alone or complexed with IGFBP-3 are also provided. Methods for increasing the level of T4 and treating or alleviating the symptoms of subjects with disorders characterized by low levels of T3 or T4 by administering effective amounts of IGF or mutant IGF alone or complexed with IGFBP-3 are additionally provided.

3 Claims, No Drawings

OTHER PUBLICATIONS

Bayne et al., "The roles of tyrosines 24, 31, and 60 in the high affinity binding of insulin–like growth factor–I to the type I insulin–like growth factor receptor" *J. Biol. Chem.* (1990) 265:15648–15652.

Bennett et al., "A double blind placebo controlled study of growth hormone therapy in fibromyalgia" *J. Musculoskeletal Pain* (1995) Abstract enclosed from Supplement: Myopain '95, Jul. 30–Aug. 3, 1995, San Antonio, Texas, p. 110.

Blum et al., "Plasma IGFBP–3 levels as clinical indicators" *Modern Concepts in Insulin–Like Growth Factors* (1991) E. M. Spencer, ed., Elsevier, New York, pp. 381–393.

Cascieri et al., "Mutants of human insulin–like growth fator I with reduced affinity for the type I insulin–like growth factor receptor" *Biochemistry* (1988) 27:3229–3233.

Cascieri et al., "Structural analogs of human insulin–like growth facotr (IGF) I with altered affinity for Type 2 IGF receptors" *J. Biol. Chem.* (1989) 264:2199–2202.

Castro–Alamancos et al., "Learning of the conditioned eye––blink response is impaired by an antisense insulin–like growth factor I oligonucleotide" *Proc. Natl. Acad. Sci. USA* (1994) 91:10203–10207.

Castro–Alamancos et al., "Long–term depression of glutamate–induced γ–aminobutyric acid release in cerebellum by insulin–like growth factor I" *Proc. Natl. Acad. Sci. USA* (1993) 90:7386–7390.

Chuzel et al., "Transcriptional regulation of the lutropin/human choriogonadotropin receptor and three enzymes of steroidogenesis by growth factors" *Eur. J. Biochem.* (1996) 239:8–16.

Ciavatta et al., "Mouse model of human $\beta^0$ thalassemia: Targeted deletion of the mouse $\beta^{maj}$– and $\beta^{min}$–globin genes in embryonic stem cells" *Proc. Natl. Acad. Sci. USA* (1995) 92:9259–9263.

Daynes et al., "Altered regulation of IL–6 production with normal aging" *J. Immunol.* (1993) 150:5219–5230.

*Diagnostic and Statistical Manual of Mental Disorders, Fourth Edition: DSM–IV™*, American Psychiatric Association, Washington, D.C. Title page and table of contents.

Ferraccioli et al., "Somatomedin C (insulin–like growth factor 1) levels decrease during acute changes of stress related hormones. Relevance for fibromyalgia" *J. Rheumatol.* (1994) 21:1332–1334.

Flood et al., "Memory–enhancing effects in male mice of pregnenolone and steroids metabolically derived from it" *Proc. Natl. Acad. Sci. USA* (1992) 89:1567–1571.

Flood et al., "Pregnenolone sulfate enhances post–training memory processes when injected in very low doses into limbic system structures: The amygdala is by far the most sensitive" *Proc. Natl. Acad. Sci. USA* (1995) 92:10806–10810.

Geders et al., "The effect of cisapride on segmental colonic transit time in patients with spinal cord injury" *Am. J. Gatroenterol.* (1995) 90:285–289.

Holsboer et al., "Steroid effects on central neurons and implications for psychiatric and neurological disorders" *Ann. N.Y. Acad. Sci.* (1994) 746:345–361.

Huang et al., "Suppression of the hypothalamus–pituitary somatotrope axis in men with spinal cord injuries" *Metabolism* (1995) 44:1116–1120.

Kahn et al., "Loss of high–affinity prostacyclin receptors in platelets and the lack of prostaglandin–induced inhibition of platelet–stimulated thrombin generation in subjects with spinal cord injury" *Proc. Natl. Acad. Sci. USA* (1996) 93:245–249.

Kamikubo et al., "Similar nuclear factors mediate stimulation of rat thyroglobulin gene transcription by thyrotropin and insulin–like growth factor–1" *Mol. Endocrinol.* (1990) 4:2021–2029.

Katagiri et al., "The role of cytochrome $b_5$ in the biosynthesis of androgens by human P450c17" *Arch. Biochem. Biophys.* (1995) 317:343–347.

Moldofsky et al., "Musculoskeletal symptoms and non–REM sleep disturbance in patients with 'Fibrositis Syndrome' and healthy subjects" *Psychosom. Med.* (1975) 37:341–351.

Mondadori et al., "Delayed emergence of effects of memory–enhancing drugs: Implications for the dynamics of long–term memory" *Proc. Natl. Acad. Sci. USA* (1994) 91:2041–2045.

Morales et al., "Effects of replacement dose of dehydroepiandrosterone in men and women of advancing age" *J. Clin. Endrocrinol. Metab.* (1994) 78:1360–1367.

Nathorst–Böös et al., "Elective ovarian removal and estrogen replacement therapy—effects on sexual life, psychological well–being and androgen status" *J. Psychosom. Obstet. Gynaecol.* (1993) 14:283–293.

Nathorst–Böös et al., "Is sexual life influenced by transdermal estrogen therapy?" *Acta Obstet. Gynecol. Scand.* (1993) 72:656–660.

Popp et al., "Hematology of a murine β–thalasesemia: A longitudinal study" *The New York Acad. Sci.* (1985) 445:432–444.

Radulescu, R.T., "Nuclear localization signal in insulin–like growth factor–binding protein type 3" *Trends Biochem. Sci.* (1994) 19(7):278.

Resnicoff et al., "Rat glioblastoma cells expressing an antisence RNA to the insulin–like growth factor–1 (IGF–1) receptor are nontumorigenic and induce regession of wild–type tumors" *Cancer Res.* (1994) 54:2218–2222.

Rinderknecht et al., "Polypeptides with nonsuppressible insulin–like and cell–growth promoting activities in human serum: Isolation, chemical characterization, and some biological properties of forms I and II" *Proc. Natl. Acad. Sci. USA* (1976) 73:2365–2369.

Robel et al., "Dehydroepiandrosterone (DHEA) is a neuroactive neurosteroid" *Ann. N.Y. Acad. Sci.* (1995) 774:82–110.

Shetty et al., "Hyposomatomedinemia in quadriplegic men" *Am. J. Med. Sci.* (1993) 305:95–100.

Sommer et al., "Molecular genetics and actions of recombinant insulin–like growth factor binding protein–3" *Modern Concepts of Insulin–Like Growth Factors* (1991) E.M. Spencer, ed., Elsevier, New York, pp. 715–728.

Tallis, Primary hypothyroidism: A case for vigilance in the psychological treatment of depression *Brit. J. Clin. Psychol.* (1993) 32:261–270.

Tsitouras et al., "Serum testosterone and growth hormone/insulin–like growth factor–1 in adults with spinal cord injury" *Horm. Metab. Res.* (1995) 27:287–292.

Wolfe et al., "The American College of Rheumatology 1990 criteria for the classfication of fibromyalgia" *Arthritis Rheum.* (1990) 33:160–172.

Yang et al., "A mouse model for $\beta^0$–thalassemia" *Proc. Natl. Acad. Sci. USA* (1995) 92:11608–11612.

Yasin et al., "Melatonin and its analogs inhibit the basal and stimulated release of hypothalamic vasopressin and oxytocin in vitro" *Endocrinol.* (1993) 132:1329–1336.

Zhou et al., "Exposure to physical and psychological stressors elevates plasma interleukin 6: Relationship to the activation of hypothalamic–pituitary–adrenal axis" *Endocrinol.* (1993) 133:2523–2530.

Carroll et al., "The effect of growth hormone replacement on the biochemical, body composition and psychological profiles of deficient adults" *Journal of Endocrinology* 148:P252 (1996).

Flood et al., "Dehydroepiandrosterone and its sulfate enhance memory retention in mice" *Chemical Abstracts* 108(25):216528 (1988).

Hesse et al., "Insulin–like growth factor I correlations to changes of the hormonal status in puberty and age" *Exp. Clin. Endocrinol.* 102(4):289–298 (1994).

Hussain et al., "Insulin–like growth factor–I alters peripheral thyroid hormone metabolism in humans: comparison with growth hormone" *Eur. J. Endocrinol.* 134(5):563–567 (1996).

Huybrechts et al., "Effect of recombinant human insulin–like growth factor–I on weight gain, fat content and hormonal parameters in broiler chickens" *Chemical Abstracts* 116(15):150581 (1992).

Kuhn et al., "Insulin–like growth factor (IGF–1), IGF–binding protein III and growth hormone in major depression" *Pharmacopsychiatry* 28(5):195 (1995).

L'Allemand et al., "Insulin–like growth factors enhance steroidogenic enzyme and corticotropin receptor messenger ribonucleic acid levels and corticotropin steroidogenic responsiveness in cultured humanadrenocortical cells" *J. Clin. Endocrinol. Metab.* 81(11):3892–3897 (1996).

Miyamoto et al., "Effects of neurosteroids on the impaired memory retention of aged C57BL/6J mice" Database Embase, Elsevier Science Publishers, Amsterdam NL, Abs. Acess. No. 96314452.

Mooney et al., "Insulin–like growth factor (IGF–1) increases working memory in aged animals" *Society for Neuronscience Abstracts* 22(1–3):1237 (1996).

Pergola et al., "Insulin–like growth factor–1 (IGF–1) and dehydroepiandrosterone sulphate in obese women" *Int. J. Obes.* 17(8):481–483 (1993).

Trung et al., "Effects of insulin–like growth factor I (IGF–I) on enzymatic activity in human adrenocortical cells. Interactions with ACTH" *J. Steroid Biochem. Mol. Biol.* 39(6):903–909 (1991).

Wolkowitz et al., "Dehydroepiandrosterone (DHEA) treatment of depression" Database Medline, Abs. Acess. No. 97177429.

Goodman & Gilman's The Pharmacological Basis of Therapeutics, 9th ed. McGraw–Hill, N.Y. pp. 1422–1423, 1996.

METHOD FOR TREATING LOW CIRCULATING LEVELS OF SEX HORMONE STEROIDS ASSOCIATED WITH AGING USING IGF OR IGF/IGFBP-3

This application is a continuation-in-part of U.S. patent application Ser. No. 08/837,603, filed Apr. 21, 1997, now pending, which is a continuation-in-part of U.S. patent application Ser. No. 08/805,807, filed Feb. 25, 1997, now pending, each of which is incorporated by reference in its entirety.

FIELD OF THE INVENTION

The invention relates generally to the field of treating psychological and metabolic disorders, and relates particularly to the treatment of these disorders by administering insulin-like growth factor (IGF) alone or complexed with insulin-like growth factor binding protein-3 (IGFBP-3).

BACKGROUND OF THE INVENTION

DHEA

Dehydroepiandrosterone (DHEA) and its sulfated form, dehydroepiandrosterone-sulfate (DHEAS) are the principal circulating steroids in humans. These two steroids are synthesized in the adrenal cortex and are normally found at about a 1:1000 molar ratio in serum. DHEAS is thought to be the storage form of DHEA, and can be converted to DHEA by the action of a sulfatase. DHEA can serve as a substrate for the production of androgenic steroids, both in the steroidogenic organs (adrenal glands, gonads and placenta) and in peripheral tissues, such as the skin, liver and brain.

DHEA is synthesized from pregnenolone in a two step reaction by cytochrome P450c17 (CYP17). CYP17 has both 17α-hydroxylase activity (which converts pregnenolone into 17α-hydroxypregnenolone, which is a cortisol precursor) and 17,20-lyase activity (which converts 17α-hydroxypregnenolone to DHEA). Purified CYP17 has very low 17,20-lyase activity. However, addition of cytochrome b5 enhances the 17,20-lyase activity of cytochrome P450c17, resulting in increased production of DHEA from pregnenolone and decreased production of cortisol (Katagiri et al. (1995) *Arch. Bioch. Biophys.* 317(2):343–347). IGF-I has been reported to increase transcription of the CYP17 gene in cultured Leydig cells, although expression of the 3β-hydroxysteroid dehydrogenase gene (which encodes an enzyme involved in the conversion of DHEA into androgenic steroids and 17α-hydroxypregnenolone into cortisol) was not affected. Insulin-like growth factor I (IGF-I) also increases choriogonadotropin-stimulated production of testosterone by Leydig cells (Chuzel et al. (1996) *Eur. J. Biochem.* 239:8–16).

DHEA and DHEAS levels normally peak in the second or third decade of life, declining by 80% or more of peak levels by age 70. Low levels of DHEA and DHEAS are associated with a variety of disease conditions, including Alzheimer's Disease and cardiovascular disease. U.S. Pat. No. 5,527,789 to Nyce suggests that high levels of DHEA (such as those caused by administration of DHEA or DHEAS) can cause cardiovascular disease due to depletion of cardiac ubiquinone, but Aberg et al. ((1996) *Chem. Biol. Interact.* 99(1–3):205–218) shows that cardiac ubiquinone levels are unaffected by DHEA administration.

DHEA and its derivatives have been described as treatments for a wide variety of conditions, including memory dysfunction, prostatic hypertrophy, immune dysfunction, alopecia, for inhibiting platelet aggregation, and minor and major depression as well preventatives for cancer and cardiovascular disease (U.S. Pat. Nos. 4,835,147, 5,077,284, 5,407,684, 5,162,198, 5,407,927, and 5,527,789 and International Patent Application No. WO 94/16709). DHEA is also known to increase REM sleep in rats and humans, suggesting its utility for the treatment of sleep disorders,, memory loss and age-related dementia (Robel and Baulieu (1995) *Ann. NY Acad. Sci.* 774:82–110).

Administration of DHEA has been reported to increase serum levels of IGF-I (U.S. Pat. No. 5,407,927; Morales et al. (1994) *J. Clin. Endocrinol. Metab.* 78(6):1360–1367) and to increase the sense of well-being, but not the libido, of subjects receiving DHEA. However, these reports do not establish any linkage between the elevation of IGF-I levels and an improved sense of well-being.

Direct administration of DHEA, DHEAS and their derivatives can lead to serious side effects. For example, acne, hair loss, hirsutism and deepening of the voice have been reported with use of DHEA in women. In men, excess DHEA may stimulate the growth of prostatic cancer. Thus, gratuitous addition of these steroid hormones individually to the circulation has been shown to be complicated in practice. Direct administration of pharmacological amounts of DHEA and/or DHEAS may cause a hormonal imbalance, which may in turn cause the side effects associated with DHEA and DHEAS administration.

Thyroid hormones

The thyroid hormones, triiodothyronine (T3) and tetraiodothyronine (T4) are major metabolic regulators in mammals. T4 is less active than T3, and can be converted to T3 in peripheral tissues. Administration of T4 or T3 increases metabolism, erythropoiesis, bone turnover and the rate of muscle relaxation. Although thyroid hormones increase the rate of protein synthesis, hyperthyroidism is associated with weight loss and muscle wasting. Hypothyroidism can be accompanied by lethargia, decreased pulmonary function (hypoventilation), low cardiac output, and decreased renal output. The thyroid hormones also interact with other endocrine hormones, including the growth hormone axis and steroidal hormones.

T4 and T3 are synthesized from thyroglobulin, a protein that is iodinated on its tyrosine residues. Two iodinated tyrosines are condensed to form a molecule of T4 or T3. Thyroglobulin, which is stored extracellularly in the follicular lumen of the thyroid gland, acts as a storage molecule for the iodinated tyrosine residues. Iodinated tyrosine residues are released from thyroglobulin by intracellular proteolysis in thyroid cells. IGF-I has been shown to increase transcription of thyroglobulin in FRTL-5 (rat thyroid) cells (Kamikubo et al. (1990) *Mol. Endocrinol.*, 4:2021–2029). The influence of increased levels of thyroglobulin mRNA on T4 and T3 levels is, however, unknown.

IGF

IGF-I and IGF-II are growth factors that have related amino acid sequence and structure, with each polypeptide having a molecular weight of approximately 7.5 kilodaltons (Kd). IGF-I mediates the major effects of growth hormone, and thus is the primary mediator of growth after birth. IGF-I has also been implicated in the actions of various other growth factors, since treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division) and/or are trophic (promote recovery/survival) for cells in neural, muscular, reproductive, skeletal and other tissues.

Unlike most growth factors, IGFs are present in substantial quantity in the circulation, but only a very small fraction of this IGF is free in the circulation or in other body fluids. Most circulating IGF is bound to the IGF-binding protein IGFBP-3. IGF-I may be measured in blood serum to diagnose abnormal growth-related conditions, e.g., pituitary gigantism, acromegaly, dwarfism, various growth hormone deficiencies, and the like. Although IGF-I is produced in many tissues, most circulating IGF-I is believed to be synthesized in the liver.

IGF is known to bind to at least three different cellular receptors; the type 1 IGF receptor, the type 2 IGF receptor, and the insulin receptor (to which IGF binds with much lower affinity than the type 1 or 2 receptor). Mutants of IGF-I have been described which have altered binding to one or more of these cellular receptors. Mutations at residue 24 (normally tyrosine) to non-aromatic residues or replacement of residues 28–37 selectively affects binding to the type 1 receptor, while mutations at residues 49–51 can selective reduce type 2 receptor binding. Mutations at residue 60 (from tyrosine to non-aromatic amino acids) can alter binding to the type 1 and 2 IGF receptors as well as the insulin receptor (Cascieri et al. (1988) *Biochemistry* 27:3229–3233; Cascieri et al. (1989) *J. Biol. Chem.* 264:2199–2202; Bayne et al. (1988) *J. Biol. Chem.* 264:11004–11008; Bayne et al. (1990) *J. Biol. Chem.* 265:15648–15652).

Almost all IGF circulates in a non-covalently associated ternary complex composed of IGF-I or IGF-II, IGFBP-3, and a larger protein subunit termed the acid labile subunit (ALS). The IGF/IGFBP-3/ALS ternary complex is composed of equimolar amounts of each of the three components. ALS has no direct IGF binding activity and appears to bind only to the IGF/IGFBP-3 binary complex. The IGF/IGFBP-3/ALS ternary complex has a molecular weight of approximately 150 Kd. This ternary complex is thought to function in the circulation "as a reservoir and a buffer for IGF-I and IGF-II preventing rapid changes in the concentration of free IGF" (Blum et al., pp. 381–393, MODERN CONCEPTS IN INSULIN-LIKE GROWTH FACTORS (E. M. Spencer, ed., Elsevier, N.Y., 1991).

Some mutant IGF-Is exhibit altered binding to IGFBP-3 and/or alterations in the ability to form the ternary complex. For example, mutations at residues 3, 4, 8, 9, 12, 15, 16 and 24 (B domain mutants) and mutations at residues 49–51 reduce formation of the binary complex, while mutations involving residues 55 and 56, as well as IGF-I where residues 63–70 (1–62 IGF-I) were deleted or residues 28–37 were replaced with a $Gly_4$ linker (1-27-$Gly_4$-38-70 IGF-I) or where both changes were made (1-27-$Gly_4$-38-62 IGF-I)) and mutants thereof (for example, 1-62 IGF-I where residue 24 was also changed) actually have increased binding to IGFBP-3. Some of these mutants, particularly the 1–62 IGF-I with a mutation at residue 24, have a reduced capacity for formation of the ternary complex, even though formation of the binary complex is increased (Baxter et al. (1992) *J. Biol. Chem.* 267:60–65).

Nearly all of the IGF-I, IGF-II and IGFBP-3 in the circulation is in complexed form, so very little free IGF is detected. Moreover, a high level of free IGF in blood is undesirable. High blood levels of free IGF would lead to serious hypoglycemia due to the insulin-like activities of IGF. In contrast to the IGFs and IGFBP-3, there is a substantial pool of free ALS in plasma which assures that IGF/IGFBP-3 complex entering the circulation immediately forms the ternary complex.

IGFBP-3 is the most abundant IGF binding protein in the circulation, but at least five other distinct IGF binding proteins (IGFBPs) have been identified in various tissues and body fluids. Although these proteins bind IGFs, they each originate from separate genes and have unique amino acid sequences. Thus, the binding proteins are not merely analogs or derivatives of a common precursor. Unlike IGFBP-3, the other IGFBPs in the circulation are not saturated with IGFs. Moreover, none of the IGFBPs other than IGFBP-3 can form the 150 Kd ternary complex.

IGF-I and IGFBP-3 may be purified from natural sources or produced by recombinant means. For instance, purification of IGF-I from human serum is well known in the art (Rinderknecht et al. (1976) *Proc. Natl. Acad. Sci. USA* 73:2365–2369). Production of IGF-I by recombinant processes is shown in EP 0 128 733, published in December of 1984. IGFBP-3 may be purified from natural sources using a process such as that shown in Baxter et al. (1986, *Biochem. Biophys. Res. Comm.* 139:1256–1261). Alternatively, IGFBP-3 may be synthesized by recombinantly as discussed in Sommer et al., pp. 715–728, MODERN CONCEPTS OF INSULIN-LIKE GROWTH FACTORS (E. M. Spencer, ed., Elsevier, N.Y., 1991). Recombinant IGFBP-3 binds IGF-I in a 1:1 molar ratio.

Topical administration of IGF-I/IGFBP-3 complex to rat and pig wounds is significantly more effective than administration of IGF-I alone (Id.). Subcutaneous administration of IGF-I/IGFBP-3 complex to hypophysectomized, ovariectomized, and normal rats, as well as intravenous administration to cynomolgus monkeys, "substantially prevents the hypoglycemic effects" of IGF-I administered alone (Id.).

IGF has been proposed as a treatment for a wide variety of indications. U.S. Pat. Nos. 5,434,134, 5,128,320, 4,988, 675, 5,106,832, 5,534,493, 5,202,119 and 5,273,961 and have disclosed the use of IGF for the treatment of cardiomyopathy and myocardial infarction, steroid-induced catabolism, type II (insulin resistant) diabetes, renal disorders, pancreatic disorders, for increasing humoral immune response and for prevention of acute renal failure, respectively. Additionally, European Patents Nos. EP 434 625, EP 436469 and EP 560 723 and International Patent Applications Nos. WO 93/23071, WO 91/12018, WO 92/00754, WO 93/02695 and WO 93/08826 disclose the use of IGF for the treatment of bone disorders, type I juvenile or insulin-responsive) diabetes and gastrointestinal disorders.

The use of IGF complexed with IGFBP-3 has also been described for use in the treatment of a variety of conditions. U.S. Pat. Nos. 5,200,509, 5,187,151, 5,407,913, and 5,527, 776 disclose the use of IGF/IGFBP-3 complex for the treatment of osteoporosis, for inducing an anabolic state when given by subcutaneous bolus injection, for increasing tissue repair when given systemically, and for treating anemia. International Patent Applications Nos. WO 95/03817, WO 95/08567, WO 95/13823, WO 95/13824, WO 96/02565 disclose the use of IGF/IGFBP-3 complex for the treatment of disorders of the reproductive, immunologic, neural, renal, and skeletal systems.

In addition to its activities in other organ systems, IGF has trophic effects on the cells of the peripheral and central nervous system. IGF's trophic effects on neural cells include promoting the survival of a variety of neuronal cell types as well as promoting neurite outgrowth in motor neurons. U.S. Pat. Nos. 5,093,317, 5,420,112, 5,068,224, and International Patent Applications Nos. WO 93/02695, WO 93/08826 and WO 95/13823 describe the use of IGF or IGF complexed to IGFBP-3 for the treatment of disorders of the nervous system, exploiting IGF's trophic activity on the cells of nervous tissues. None of these patents or publications disclose or suggest the use of IGF for the treatment of psychological disorders or memory loss.

Other disorders exist which would benefit from a reduction in the levels of IGF. For example, some cancer cells are dependent on IGF for continued survival (Resnicoff et al. (1994) *Cancer Res.* 54:2218–2222). Reduction in circulating IGF levels could result in tumor progression, as IGF-dependent tumor cells undergo apoptosis. In autoimmune disorders, reduction in IGF levels could reduce symptoms of these disorders, as IGF is known to have stimulatory effects on the immune system.

None of the references disclosed above disclose or suggest the use of IGF or IGF/IGFBP-3 complex for the treating or alleviating the symptoms of psychological or metabolic disorders. Further, none of the cited references disclose or suggest the administration of IGF or IGF/IGFBP-3 complex for treating or alleviating the symptoms of sleep disorders or for treating or alleviating symptoms and disorders associated with sexual senescence.

Psychological Disorders

The acuity of memory gradually declines with age, and can also be affected by a variety of disorders. Memory can be characterized in various ways, including declarative or explicit (involving recall and recognition) versus implicit (involving skills and conditioning). A number of compounds have been suggested as treatments for enhancing memory, including cholinergic agonists and cholinesterase inhibitors, calcium channel blockers, angiotensin convertring enzyme (ACE)-inhibitors such as captopril and peptides such as vassopressin and corticotropin (which induce the synthesis of adrenal steroids), and others (Mondadori et al. (1994) *Proc. Natl. Acad. Sci. USA* 91: 2041–2045). Steroid hormones have also been used to treat memory loss. Administration of pregnenolone sulfate (PS), dehydroepiandrosterone sulfate (DHEAS), androstenedione (A), testosterone and aldosterone (among others) were effective in improving retention in a rodent model (Flood et al. (1992) *Proc. Natl. Acad. Sci. USA* 89: 1567–1571). PS and DHEAS were active as memory enhancers when injected into the hippocampus. PS was also active when injected into the amygdala and mammillary bodies but not the caudate nucleus (Flood et al. (1995) *Proc. Natl. Acad. Sci. USA* 92: 10806–10810). Pregnenolone and DHEA are believed to act in a paracrine fashion at neurons, thus modifying sleep EEG in humans in a manner that suggests their potential as memory enhancers (Holsboer et al. (1994)*Ann. NY Acad. Sci.* 746: 345–361).

IGF-I has been shown to induce long term depression of glutamate-induced gamma-aminobutyric acid release in the cerebellum (Castro-Alemancos et al. (1993) *Proc. Natl. Acad. Sci. USA* 90: 7386–7390). This finding led Castro-Alemancos et al. to test the effects of IGF-I on motor learning and retention (i.e., implicit memory), using the "eye-blink response" as the indicator. Experimental results led them to postulate that IGF-I plays a role in learning the eye-blink response but they found no evidence for a role for IGF-I in retention or memory (Castro-Alemancos et al. (1994) *Proc. Natl. Acad. Sci.* USA 91: 10203–10207).

There is a need in the art for an effective method for enhancing memory and for treating and/or alleviating the symptoms of memory loss.

Depressive disorders are common among the population. Seventeen percent of the population is expected to suffer from major depression during their lifetime prevalence (Andrews et al. (1994) *Am. J. Med.* 97:24S–32S). Approximately two-thirds of patients respond to antidepressant medication. Nevertheless, all effective classes of antidepressants have significant side-effect profiles. Selective serotonin reuptake inhibitors (SSRIs) cause nausea, headache and sexual dysfunction.

Additionally, many SSRIs inhibit a number of hepatic cytochrome P450 isozymes which can lead to serious drug interaction problems in addition to the side effects caused directly by the drugs themselves. Tricyclics are cardiotoxic and overdoses are frequently fatal. Other classes can cause seizures, priapism and elevations in blood pressure (Andrews et al. (1994) *Am. J Med.* 97: 24S–32S).

Primary hypothyroidism is a relatively common endocrine disorder that develops insidiously and can mimic depression. Between and 8 and 14 percent of patients diagnosed with depression have some degree of hypothyroidism (Tallis (1993) *Brit. J. Clin. Psychol.* 32:261–270). Primary hypothyroidism may be treated by increasing levels of T4 and/or T3.

There is a need in the art for a method for treating and/or alleviating the symptoms of depression of multiple etiologies.

Metabolic Disorders

Spinal chord injury (SCI) in adult males may result in various hormonal and metabolic abnormalities—both as a result of injury and secondary to reduced exercise and mobility. Various studies in this patient population have documented the following abnormalixties in subjects with SCI relative to the normal population:

a suppression in the GH response to growth hormone releasing hormone (GHRH), arginine or other agents; significantly lower IGF-I levels; elevated follicle stimulating hormone (FSH) and leutinizing hormone (LH) levels; reduced thyroid hormone levels; hyperprolactinemia (in quadriplegics only); hypogonadism associated with lowered testosterone levels; increased frequency of urinary tract infections; obesity; high prevalence of carbohydrate intolerance; diabetes; low HDL cholesterol; lowered cardiopulmonary fitness and dyspnea at rest; increased susceptibility to coronary artery disease; deficient bowel control (esp. constipation); lower resting metabolic rate; and active pressure sores (Shetty et al. (1993) *Am J. Med Sci.* 305:95–100; Huang et al. (1995) *Metabolism* 44:1116–20; Tsitouras et al. (1995) *Horm. Metab. Res.* 27:287–292; Geders et al. (1995) *Am. J. Gastroenterol* 90:285–289; Bauman et al. (1994) *Metabolism* 43:749–756; Bauman et al. (1994) *J. Clin. Endocrinol. Metab.* 78:1135–1138; Almenoff et al. (1995) *Paraplegia* 33:274–277; Bauman et al. (1994) *Horm. Metab. Res.* 26:152–156; Kahn et al. (1996) *Proc.Natl.Acad.Sci.* USA 93:245–249).

Atelectasis (insufficient lung inflation/deflation) and pneumonia are the major causes of morbidity and mortality in patients with SCI (cited in Almenoff et al., supra). In a study of 165 SCI subjects, forced vital capacity and other measures of pulmonary function were inversely correlated with with the level of injury (i.e., the higher the level of injury, the lower the parameter; Almenoff et al. (1995) *Lung* 173:297–306). Other studies have shown that thyroid hormone (both T3 and T4) levels are significantly lower in quadriplegics than in paraplegics or normal subjects (Huang et al., supra). Thyroid hormone levels are correlated with pulmonary function. Further, hypothyroid individuals are known to suffer from breathing difficulties.

Most of the metabolic abnormalities experienced by SCI victims are also increasingly observed during the normal aging process in humans. For this reason, SCI may provide an excellent model for the study of the normal aging process as well as premature aging (Bauman et al. (1994) *Horm. Metab. Res.*, supra). There are also several genetic diseases which cause premature aging, including ataxia telangiectasia, Werner's syndrome, Hutchinson-Guilford progeria, and Cockayne's syndrome. It is expected that symptoms that are shared between SCI, aging and premature aging would benefit from the same treatment.

Accordingly, there is a need in the art for an effective treatment for alleviating symptoms associated with SCI and for the symptoms of aging and premature aging.

Stress hormones can profoundly affect the workings of all endocrine subsystems, resulting in a condition referred to as hypothalamic-pituitary axis dysregulation (HPA dysregulation). For example, individuals under stress do not experience the normal increase in growth hormone levels following induction of hypoglycemia (induced by administration of insulin); instead, IGF-I levels drop and cortisol and norepinephrine levels rise (Ferraccioli et al. (1994) *J. Rheumatol.* 21:1332–1334). This abnormal response is believed to play a role in lowering IGF-I levels in chronically stressed conditions such as fibromyalgia (Id.). Fibromyalgia is a relatively common disorder with a prevalence in the general population of between 2 and 4% (Wolfe et al. (1990) *Arthritis Rheum.* 33:160–172).

Fibromyalgia, which is approximately twice as common in women as in men, is characterized by widespread pain, tenderness, fatigue, sleep disturbance, paresthesias, anxiety, and other similar symptoms. Fibromyalgia has many symptoms in common with chronic fatigue syndrome and the two conditions are frequently treated with the same drugs. Interestingly, while sleep disturbances are associated with fibromyalgia, sleep deprivation itself can induce the symptoms of fibromyalgia (Moldofsky et al. (1975) *Psychosom. Med.* 37:341–351).

Physical and psychological stressors elevate plasma levels of IL-6. The source of this IL-6 is unknown, but it has been shown to be non-immune (Zhou et al. (1993) *Endocrinol.* 133:2523–2530). DHEAS has been shown to reduce chronically elevated levels of IL-6 (Daynes et al. (1993) *J. Immunol.* 150:5219–5230).

HPA dysregulation is also observed when sleep patterns are disrupted. Melatonin inhibits the basal and stimulated release of hypothalamic vassopressin in vitro (Yasin et al. (1993) *Endocrinol.* 132:1329–1336), and sleep inhibits activation of adrenocorticotropic hormone (ACTH) and cortisol secretion. Conversely, through the mineralocorticoid (slow wave sleep) and glucocorticoid (rapid eye movement—REM—sleep) receptors, cortisol can exert feedback effects on sleep patterns (Holsboer et al. (1994) *Ann. N. Y Acad. Sci.* 746:345–361). DHEA affects the duration of REM sleep and this may explain some of its actions on the consolidation of memory.

There is a need in the art for effective methods for treating disorders associated with chronic stress and/or alleviating the symptoms of disorders associated with chronic stress.

The thalassemias are a group of genetic diseases which share the symptom of reduced levels of hemoglobin in the blood (i.e., anemia). This is due to reduced or absent production of either adult alpha or adult beta hemoglobin. The existence of thalassemia in a subject emerges during the first month of life, as fetal hemoglobin is down regulated and adult hemoglobin is up regulated. Thalassemic individuals are unable to switch over to adult hemoglobin and become anemic and dependent on transfusions. In addition to anemia, thalassemia patients also experience symptoms relating to high levels of toxic products such as iron and billrubin. Animal models, including naturally occurring mutants and introduced mutants, are available for testing treatments for beta thalassemias (Popp et al. (1984) *Proc. NY Acad. Sci.* 445:432–444; Ciavatta et al. (1995) *Proc. Natl. Acad. Sci. USA* 92:9259–9263; Yang et al. (1995) *Proc. Natl. Acad. Sci. USA* 92:11608–11612). A need exists in the art for effective methods for improving or alleviating symptoms associated with deficiencies of detoxification in thalassemia patients.

Sexual Senescence

The hypothalamic-pituitary-gonadotropic axis is responsible for the proper function of reproductive organs as well as for some aspects of reproductive behavior. Although IGF-I has been implicated in gamete formation, little is known about its effects on sexual behavior. IGF-I has been implicated in the gonadotropic axis in a study of Igf1 knock-out mice, which are infertile dwarfs with drastically reduced levels of serum testosterone (Baker et al. (1996) *Mol. Endocrinol.* 10:903–918).

Androgen levels are known to decrease with aging in men. Androgen deficiency in men has been linked to decreased muscle mass, asthenia, osteoporosis and decreased sexual activity and, in some cases, changes in mood and cognitive function. In women, studies have reported a relationship between the transition into menopause and a decline in sexual interest and activity as measured by a variety of symptoms. Estrogen can affect some (but not all) of these symptoms (Nathorst-Boos et al. (1993) *Acta Obstet. Gynecol. Scand.* 72:656–660). In one study, McCoy Sexual Rating score (which relates to parameters such as the frequency of sexual fantasies, impaired lubrication and pleasure from intercourse) correlated with levels of circulating IGF-I (Nathorst-Boos et al. (1993) *J. Psychosom. Obstet. Gynaecol.* 14:283–293).

DHEA and its derivatives have been suggested as treatments for some symptoms of sexual senescence, such as prostatic hypertrophy and sexual dysfunction associated with menopause. U.S. Pat. No. 4,835,147 teaches the administration of DHEA for the treatment of prostatic hypertrophy and sexual dysfunction symptoms related to nervous system dysfunction.

DETAILED DESCRIPTION OF THE INVENTION

Definitions

As used herein, "IGF" refers to insulin-like growth factor from any species. IGF includes both IGF-I and IGF-II, in native-sequence or variant form, including but not limited to naturally-occurring allelic variants. IGF may be from any source, whether natural, synthetic or recombinant.

As used herein, "IGF-I" refers to insulin-like growth factor I from any species, including bovine, ovine, porcine and human, in native-sequence or variant form, including but not limited to naturally-occurring allelic variants. IGF-I may be from any source, whether natural, synthetic or recombinant, provided that it will bind IGFBP-3 at the appropriate site. Preferred herein is human native-sequence, mature IGF-I, preferably without an amino-terminal methionine. More preferably, the native sequence, mature IGF-I is produced recombinantly, for example, as described in PCT publication WO 95/04076.

As used herein, the term "mutant IGF-I" refers to which have altered amino acid sequences at one or more sites in the molecule. Mutant IGF-I retains its ability to bind IGFBP-3, but may be altered in its other properties, such as binding to the type I or type II IGF receptor or binding to the insulin receptor. Descriptions of mutant IGF-Is may be found in Cascieri et al. (1988) *Biochemistry* 27:3229–3233; (1989) *J. Biol. Chem.* 264:2199–2202), Bayne et al. (1990) *J. Biol. Chem.* 265:15648–15652) and Baxter et al. (1992) *J. Biol. Chem.* 267:60–65). Examples of mutant IGF-I include mutants in which one or more of IGF-Is tyrosine residues (i.e., residues 24, 31, or 60) are replaced with non-aromatic residues (i.e., other than tyrosine, phenylalanine or tryptophan), mutants where amino acid residues 49, 50, 51, 53, 55 and 56 are altered (for example, where residues 49–50 are altered to Thr-Ser-Ile or where residues 55–56 are altered to Tyr-Gln).

As used herein, "IGF-II" refers to insulin-like growth factor II from any species, including bovine, ovine, porcine and human, in native-sequence or variant form, including but not limited to naturally-occurring allelic variants. IGF-II may be from any source, whether natural, synthetic or recombinant, provided that it will bind IGFBP-3 at the appropriate site. Preferred herein is human native-sequence, mature IGF-II, preferably without an amino-terminal methionine. More preferably, the native sequence, mature IGF-I is produced recombinantly, for example, as described in PCT publication WO 95/04076.

As used herein, "IGFBP-3" refers to insulin-like growth factor binding protein 3. IGFBP-3 is a member of the insulin-like growth factor binding protein family. IGFBP-3 may be from any species, including bovine, ovine, porcine and human, in native-sequence or variant form, including but not limited to naturally-occurring allelic variants. Prefered IGFBP-3 embodiments include native sequence human IGFBP-3 and variants of human IGFBP-3 wherein the one or more of the asparagine residues which form the normal N-linked glycosylation sites (positions 89, 109 and 172) are changed to aspartate (e.g.: N89D; N109D; N172D; N89D, N109D; N89D,N172D; N109D,N172D; and N89D,N109D, N172D variants) or to other amino acid residues (e.g.: N89X; N109X; N172X; N89X,N109X; N89X,N172X; N109X,N172X; and N89X,N109X,N172X variants) as well as variants which have been altered to improve resistance to degradation, such as alterations at positions 116 and 135 (e.g., D116E, D135E and D116E,D135E), or alterations which affect the nuclear localization signal (NLS) of IGFBP-3, which is located at residues 215 through 232 (Radulescu, 1994, *Trends Biochem Sci.* 19(7):278). Examples of preferred NLS variant IGFBP-3s include K228E, R230G, K228E,R230G, K228X, R230X, and K228X,R230X, as well as variations at residues 215, 216 and 231. Of course, a variant IGFBP-3 may include more than one type of variation (e.g., a variant IGFBP-3 may be both ND variant and degradation resistant variant). IGFBP-3 can form a binary complex with IGF, and a ternary complex with IGF and the acid labile subunit (ALS). IGFBP-3 may be from any source, whether natural, synthetic or recombinant, provided that it will bind IGF-I and ALS at the appropriate sites. Preferably, IGFBP-3 is produced recombinantly, as described in PCT publication WO 95/04076.

A "therapeutic composition," as used herein, is defined as comprising IGF-I complexed with its binding protein, IGFBP-3 (IGF-I/IGFBP-3 complex). The therapeutic composition may also contain other substances such as water, minerals, carriers such as proteins, and other excipients known to one skilled in the art.

The term "metabolic disorder," as used herein, is defined as disorders associated with deleterious alterations in metabolism. Metabolic disorders include, for example, hypothyroidism, disorders associated with chronic stress, symptoms associated with spinal cord injury such as decreased pulmonary function, increased colonic transit time and the like.

The term "psychological disorder," as used herein, includes, but is not limited to, disorders of mood and affect, memory dysfunction, motor and tic disorders, substance abuse disorders, psychotic disorders, and anxiety disorders. Psychological disorders may be recognized as described in the Diagnostic and Statistical Manual of Mental Disorders: DSM-IV (American Psychiatric Assn., Washington, D.C., 4th ed., 1994) ("DSM-IV").

Disorders of mood and affect include, for example, minor and major depression, dysthymic disorder, bipolar disorders and the like. Mood disorders are characterized in DSM-IV, and may be recognized by symptoms such as decreased energy, insomnia, weight loss, depressed mood, loss of pleasure or interest in most or all activities.

Memory dysfunctions are also referred to as amnestic disorders. Amnestic disorders are generally characterized by an inability to learn new information or to recall previously learned information. Memory dysfunctions may be the result of pathological processes (e.g., trauma, hypoxia, disease) or may be a result of the normal aging process.

Motor and tic disorders are characterized by motor and/or vocal tics, and include, but are not limited to, Tourette's disorder, chronic motor or vocal tic disorder, transient tic disorder, and stereotypic movement disorder. Tics are sudden, rapid, recurrent, nonrhythmic, stereotyped movements (motor tics) or vocalizations (vocal tics). Motor tics include eye blinking, shoulder movements such as shrugging, and facial grimacing. Vocal tics include grunts, clicks, yelps, barks, snorts, coprolalia (use of socially unacceptable words) and echolalia (repeating the last heard sound).

Substance abuse disorders include disorders such as substance dependence, substance abuse and the sequalae of substance abuse/dependence, such as substance-induced psychological disorders, substance withdrawal and substance-induced dementia or amnestic disorders. Substance abuse disorders may be recognized by impaired control of use of a substance such as alcohol, stimulants or narcotics, and may be accompanied by guilt or regret about use and failed attempts to reduce use.

Psychotic disorders include such conditions as schizophrenia, schizofreniform disorder, schizoaffective disorder, and delusional disorder. Symptoms of psychotic disorders may include, but are not limited to, delusions, hallucinations, disorganized speech (in which the patient may "slip" from one topic to another, give answers to questions that are obliquely related or not at all related to the question, or have speech so severely disorganized as to be incomprehensible), grossly disorganized behavior (that may be manifested by unpredictable agitation, difficulty in maintaining hygiene, inappropriate clothing, inappropriate sexual behavior, etc.), negative symptoms (including loss or flattening of affect, avolition, anhedonia), and catatonia.

Anxiety disorders are characterized by exessive anxiety, worry, fear, tension, or arousal that cause distress and/or a clinically significant decrease in function. Anxiety disorders include, but are not limited to, panic disorder, phobias (including agoraphobia), obsessive-compulsive disorder, and posttraumatic stress disorder. "Sexual dysfunctions," as used herein, refer to disorders or dysfunctions of sexual drive, sexual excitement and orgasm, as well as dysfunctions of male and female arousal, such as erectile and lubrication dysfunctions.

A "low level of circulating sex steroid," as used herein, refers to a serum level of a sex steroid that is in the $30$th or lower percentile for the population of the same species, sex, and approximate age (i.e., ±5 years).

"Fibromyalgia," as used herein refers to a syndrome that has been defined by the American College of Rheumatology (Wolfe et al. (1990), supra). Fibromyalgia is characterized by widespread pain of at least three months duration that is present in the axial skeleton as well as all four quadrants of the body. Pain is also elicited at at least 11 of 18 stereotypical pressure points.

MODES OF CARRYING OUT THE INVENTION

The inventors have unexpectedly found that administration of IGF/IGFBP-3 complex can increase serum levels of DHEAS, T4, estrogen, and androstenedione. While not wishing to be bound by any particular theory, the inventors propose that any disorder characterized by a deficiency of DHEA, DHEAS, thyroid hormone or sex steroids and disorders that may be treated by administration of DHEA, DHEAS thyroid hormone or sex steroids may be treated by administration of IGF, preferably IGF complexed with IGFBP-3. Symptoms of disorders characterized by a deficiency of DHEA, DHEAS, thyroid hormone or sex steroids and disorders that may be alleviated by administration of DHEA, DHEAS thyroid hormone or sex steroids may be treated by administration of IGF, preferably IGF complexed with IGFBP-3.

One embodiment of the invention is a method for increasing levels of DHEAS in an individual, by administering IGF or IGF/IGFBP-3 complex. Administration of IGF or IGF/IGFBP-3 complex increases serum levels of DHEAS.

In another embodiment, the invention relates to the use of IGF for the treatment of psychological and metabolic disorders. Psychological disorders include amnestic disorders such as memory dysfunction, disorders of mood and affect including mild and major depression, motor and tic disorders such as Tourette's disorder, substance abuse disorders including subtance abuse and substance dependence, psychotic disorders such as schizophrenia, and anxiety disorders including posttraumatic stress disorder. Administration of IGF, preferably IGF/IGFBP-3 complex results in improvements or alleviation of the symptoms of psychological disorders.

IGF or IGF/IGFBP-3 complex may be administered for the treatment of amnestic disorders, such as memory loss, particularly declarative memory loss. Declarative memory (also known as explicit memory) involves recall and recognition, as opposed to implicit memory, which relates to memory of skills and conditioning. Memory loss is associated with normal aging, as well as trauma, hypoxia and disease. Administration of IGF or IGF/IGFBP-3 complex improves memory function and alleviates the symptoms of amnestic disorders.

IGF or IGF/IGFBP-3 complex may be administered for the treatment disorders of mood and affect. IGF or IGF/IGFBP-3 complex treatment alleviates or reduces the symptoms of such mood and affect disorders as mild depression, major depression, cyclothymic disorder, dysthymic disorder, and bipolar disorder. Alleviation or reduction of symptoms of disorders of mood and affect may be indicated by improved mood, increased interest in any or all activities, reduction of feelings of guilt, or other changes as will be apparent to one of skill in the art.

In another embodiment, the invention relates to the treatment of disorders of metabolism. The symptoms of disorders of metabolism such as primary hypothyroidism, HPA axis dysregulation, and symptoms associated with spinal cord injury (SCI) are improved or alleviated by administration of IGF or IGF/IGFBP-3. Improvements in the symptoms of disorders of metabolism may include decreased lethargy, reduced cold sensitivity, improved pulmonary function, decreased colonic transit time, and other measures which will be apparent to the skilled artisan.

The invention also relates to to the treatment of disorders which result in premature aging, such as ataxia telangiectasia, Werner's syndrome, Hutchinson-Guilford progeria, and Cockayne's syndrome. The administration of IGF or IGF/IGFBP-3 results in improvements in the symptoms of premature aging.

In a further embodiment, the invention relates to the treatment of chronic stress-related conditions. Chronic stress-related conditions include fibromyalgia, chronic fatigue syndrome, hypothalamic-pituitary axis dysregulation, chronic sleep deprivation, and conditions associated with elevated levels of interleukin 6 (IL-6). Administration of IGF or IGF/IGFBP-3 complex results in reduction or alleviation of the symptoms of chronic stress-related conditions.

One embodiment relates to the use of IGF or IGF/IGFBP-3 for the treatment of sleep disorders. Administration of IGF or IGF/IGFBP-3 improves the symptoms of sleep disorders, as measured by an increase in REM sleep.

Another embodiment of the invention relates to the administration of IGF or IGFBP-3 for the treatment of the symptoms of sexual senescence. Administration of IGF or IGF/IGFBP-3 results in improvements in the symptoms of sexual senescence, such as a reduction in the symptoms of prostatic hypertrophy and improvement in sexual dysfunctions.

Administration of IGF or IGF/IGFBP-3 results in increases in circulating levels of sex hormones, such as estradiol and androstenedione. Accordingly, administration of IGF or IGF/IGFBP-3 is useful for the treatment of symptoms, disorders, and conditions associated with low circulating levels of sex steroids.

The invention also relates to increasing the detoxification capacity of a subject. The administration of IGF or IGF/IGFBP-3 is useful for increasing levels of cytochrome b5, a protein that plays important roles in the modulation and regulation of cytochrome P450 pathways. As demonstrated in Example 2, administration of IGF-I/IGFBP-3 complex increases serum levels of DHEAS without increasing levels of cortisol, indicating an increase in cytochrome b5 activity. Example 5 further shows that administration of IGF-I/IGFBP-3 complex increases levels of cytochrome b5 MRNA levels in blood cells. In addition to its activity in stimulating DHEA synthesis, cytochrome b5 regulates the detoxification functions of cytochrome P450. Therefore, administration of IGF or IGF-I/IGFBP-3 is useful for treating disorders associated with insufficient detoxification activity, such as the thalassemias and alchohol or other drug-related toxicities. Administration of IGF or IGFBP-3 results in improvement or alleviation of symptoms of thalassemia associated with accumulation of toxic products such as iron and bilirubin.

The invention also provides for new methods for the reduction of IGF activity in individuals in need of such reduction. As is shown in Example 2, administration of IGF-I/IGFBP-3 complex results in marked reductions in the level of IGF-II, accompanied by an increase in IGF-I. While not wishing to be bound to any one theory, the increased IGF-I levels are believed to be due to the IGF-I which has been administered to the subjects. This reduction in IGF-II levels can be exploited to reduced overall IGF activity in the circulation, by administering a complex of IGFBP-3 and a mutant IGF-I which has been engineered to have reduced binding to one or more of the IGF receptors (the type 1 and 2 IGF receptors and the insulin receptor), while retaining the ability to bind IGFBP-3 and form the ternary complex. Administration of a complex of this mutant IGF-I and IGFBP-3 results in a reduction in the level of active IGF in the circulation, thereby reducing the numbers and/or activity of cells and tissues which depend on IGF for survival or activity.

In one embodiment, mutant IGF/IGFBP-3 complex is administered to subjects having cancers dependent on IGF. Reduction of levels of active IGF is useful in the treatment of cancers where the cancer cells are IGF-dependent for survival. Reduction of active IGF levels results in apoptosis of the IGF-dependent cancer cells, resulting in reduction in tumor mass.

In another embodiment, mutant IGF/IGFBP-3 complex is administered to subjects having autoimmune disorders. Autoimmune disorders such as systemic lupus erythematosis ("lupus" or "SLE"), in multiple sclerosis ("MS"), Grave's disease, Hashimoto's thyroiditis, Goodpasture's syndrome, myasthenia gravis ("MG"), insulin resistance, and other disorders known in the art to involve autoimmune reactions, will benefit from the administration of mutant IGF-I complexed to IGFBP-3. Immune effector cells are known to be stimulated by IGF. Accordingly, reduction of active IGF levels will reduce the stimulation of the immune cells, resulting in improvement or alleviation of the symptoms of autoimmune disorders, In a further embodiment, mutant IGF/IGFBP-3 complex is administered to subjects having hyperthyroid conditions (i.e., excess levels of thyroid hormones). Hyperthyroid conditions will also benefit from the administration of mutant IGF-I/IGFBP-3 complex. As shown herein, the administration of IGF-I/IGFBP-3 increases levels of T4, and is useful in the treatment of hypothyroidism. Reducing circulating levels of IGF will decrease thyroid hormone levels, resulting in improvement and/or alleviation of the symptoms of hyperthyroid and other conditions where it is desirable to reduce levels of thyroid hormone.

Another embodiment involves the administration of mutant IGF/IGFBP-3 complex to subjects having conditions associated with excess levels of androgen hormones. Conditions involving an excess of androgen hormones, such as virilization, hirsutism, and other disorders known by one of skill in the art to involve elevated levels of androgen hormones, will benefit from the administration of mutant IGF-I/IGFBP-3 complex. As shown herein, the administration of IGF-I/IGFBP-3 complex results in increased levels of androgen hormones and in DHEAS, an androgen hormone precursor. Reduction of circulating IGF activity will decrease levels of androgen hormones, thereby improving or alleviating the symptoms of disorders involving excess androgen hormones or disorders where a reduction in androgen hormones is beneficial.

In a further embodiment, mutant IGF/IGFBP-3 complex is administered to subjects having hypophosphatemia (decreased serum concentrations of phosphorus). Subjects having low serum phosphorus will benefit from the administration of mutant IGF/IGFBP-3 complex. Administration of mutant IGF/IGFBP-3 complex results in increased serum phosphorus levels and improvement or alleviation of the symptoms associated with hypophosphatemia.

The inventive methods disclosed herein provide for the parenteral administration of IGF or IGF/IGFBP-3 complex to subjects in need of such treatment. Parenteral administration includes, but is not limited to, intravenous (IV), intramuscular (IM), subcutaneous (SC), intraperitoneal (IP), intranasal, and inhalant routes. IV, IM, SC, and IP administration may be by bolus or infusion, and in the case of SC, may also be by slow release implantable device, including, but not limited to pumps, slow release formulations, and mechanical devices. The formulation, route and method of administration, and dosage will depend on the disorder to be treated and the medical history of the patient. In general, a dose that is administered by subcutaneous injection will be greater than the therapeutically-equivalent dose given intravenously or intramuscularly. Preferably, the dose of IGF administered will be from about 25 $\mu$g/kg to about 2 mg/kg of body weight. More preferably, the dose of IGF will be from about 50 $\mu$g/kg to about 1 mg/kg. Most preferably the dose of IGF will be from about 100 $\mu$g/kg to about 400 $\mu$g/kg.

The IGF is preferably IGF-I. A composition comprising equimolar amounts of IGF-I and IGFBP-3 is preferred. Preferably the IGF-I and IGFBP-3 are complexed prior to administration. Preferably, the complex is formed by mixing approximately equimolar amounts of IGF-I and IGFBP-3 dissolved in physiologically compatible carriers such as normal saline, or phosphate buffered saline solution. More preferably, a concentrated solution of rhIGF-I and a concentrated solution of rhIGFBP-3 are mixed together for a sufficient time to form an equimolar complex.

Most preferably, rhIGF-I and rhIGFBP-3 are combined to form a complex during purification, as described in International Patent Application No. WO 96/40736.

Mutant IGF-I is preferably a mutant IGF-I that retains binding to IGFBP-3, but has reduced binding to one or more of the cellular receptors to which IGF-I normally binds. Preferred mutant IGF-Is that have reduced binding to all IGF cellular receptors but that retain IGFBP-3 binding include, for example: mutant IGF-Is where position 60 is altered; mutant IGF-Is where position 60 and other positions are altered, such as positions 24, 31, 55 and 56. Preferred mutant IGF-Is that have reduced type 1 IGF receptor binding but retain IGFBP-3 binding include mutant IGF-Is with changes at position 24 and 31. Preferred mutant IGF-Is that have reduced type 2 IGF receptor binding but retain IGFBP-3 binding include mutations at positions 41, 45, and 46.

For parenteral administration, compositions of the complex may be semi-solid or liquid preparations, such as liquids, suspensions, and the like. Physiologically compatible carriers include, but are not limited to, normal saline, serum albumin, 5% dextrose, plasma preparations, and other protein-containing solutions. Optionally, the carrier may also include detergents or surfactants.

EXAMPLES

Example 1 rhIGF-I and rhIGF-I/IGFBP-3 complex were administered to ovariectomized mature rats, and the effects on an endocrine organ, the adrenal gland, were measured.

16 week old female Sprague-Dawley rats were obtained from Charles-Rivers Laboratories and allowed to acclimate at least one week prior to ovariectomy. Animals were housed separately in accordance with NIH guidelines, and allowed ad libitum access to Purina® brand Rat Laboratory Chow 5001 and water. Animals were ovariectomized bilaterally, using a dorsal approach. Following ovariectomy, animals were allowed an eight week recovery period, then randomly assigned to the treatment groups shown in Table 1. rhIGF-I and rhIGF-I/IGFBP-3 complex (produced as described in Sommer et al., supra) diluted in phosphate buffered saline (20 mM sodium phosphate, pH 6.0, 150 mM NaCl in pyrogen-free water) were administered to the test animals by daily subcutaneous injection. Control animals received daily subcutaneous injections of phosphate-buffered saline. Animals were euthanized immediately following the completion of eight weeks of treatment.

Adrenal weights and body weights were measured for all animal groups at sacrifice. Relative adrenal weights were calculated by dividing the adrenal weight (mg) by the body weight (kg) for each animal. The results are shown in Table 1.

TABLE 1

| TREATMENT | n | MEAN ± SD | p value* |
|---|---|---|---|
| OVX Controls | 11 | 132.7 ± 36.9 | — |
| IGF-I (0.9 mg/Kg) | 7 | 147.1 ± 22.8 | 0.3216 |
| IGF-I (2.6 mg/Kg) | 7 | 161.4 ± 47.8 | 0.2043 |
| IGF-I groups combined | 14 | 154.3 ± 36.7 | 0.1607 |
| IGF-I complex (0.9 mg/Kg**) | 8 | 172.5 ± 36.2 | 0.0327 |
| IGF-I complex (2.6 mg/Kg**) | 8 | 160.0 ± 22.7 | 0.0634 |
| IGF-I complex gps combined | 16 | 166.3 ± 29.9 | 0.0219 |

*versus OVX control group; two-tailed, unpaired t-test;
**equivalent IGF-I dose present in ca. 1:4 ratio to IGFBP-3 binding protein.

These results show that systemic administration of IGF complex increases adrenal tissue weight significantly, relative to body weight. It might be reasonably be assumed from these data that adrenal function would also be affected by IGF complex administration.

The results also show that an equivalent dose of IGF-I administered in the form of a complex with its binding protein, IGFBP-3, is superior in its effect on adrenal tissue when compared with the same dose of IGF-I alone.

Example 2

18 healthy male and female volunteers (ages 20–53) were treated with rhIGF-I/IGFBP-3 at doses of 0, 0.3, 1.0 or 3.0 mg/kg administered daily by intravenous infusion (15 minute infusion). rhIGF-I/IGFBP-3 (manufactured as described in Sommer et al., supra) dissolved in 50 mM sodium acetate, 105 mM sodium chloride, pH 5.5, was diluted with normal (0.9%) saline. Serum samples taken at various times before, during and after treatment were assayed for levels of various endocrine factors. To establish baseline values, samples taken just prior to the first dose, or a day earlier, were assayed. Samples taken on day 6 or 7 (in each case, 24 hours after the previous dose of rhIGF-I/IGFBP-3 had been administered) were used in the assays for comparison, and expressed as a percentage of baseline. In this way, the circulating levels of various endocrine substances were determined for each patient at the beginning and at (or near) the end of the rhIGF-I/IGFBP-3 treatment regimen in order to assess the effect of IGF-I complex administration.

Assays were performed using commercial kits according to each manufacturer's instructions: Nichols Institute Diagnostics, San Juan Capistrano, Calif. (DHEAS, Cortisol, LH, Erythropoietin, Calcitonin, Intact parathyroid hormone (PTH), active Renin, Total T4, Free T4, thyroglobulin, thyroid stimulating hormone(TSH)); Diagnostics Systems Laboratories, Webster, TX (Prolactin, IGFBP-2, aldosterone, androstenedione, total T3, testosterone, estradiol); Biotecx Laboratories, Inc., Houston, TX (thyroid binding globulin (TBG)).

In addition, some assays (IGF-I, IGF-II, IGFBP-3, CBG, SHBG, DHEA, Osteocalcin, Procollagen Peptides, Bone Alkaline Phosphatase) were performed under contract by Endocrine Sciences, Calabasas Hills, Calif.

The results are summarized in Table 2.

TABLE 2

| ASSAY | Placebo | 0.3 mg/kg | 1.0 mg/kg | 3.0 mg/kg | Treatment* |
|---|---|---|---|---|---|
| IGF-I | 91.83 ± 7.78 | 150.25 ± 21.1 (0.0084) | 183.5 ± 43.27 (0.0228) | 202.67 ± 28.0 (0.0176) | 176.64 ± 36.8 (0.00001) |
| IGF-II | 111.83 ± 29.8 | 67.25 ± 6.24 (0.0134) | 57.5 ± 6.03 (0.0058) | 42.0 ± 6.25 (0.0017) | 56.82 ± 11.83 (0.0051) |
| IGFBP-2 | 92.17 ± 29.43 | 159.0 ± 30.22 (0.012) | 189.25 ± 60.2 (0.0404) | 167.7 ± 123.9 (0.4042) | 172.36 ± 68.0 (0.0043) |
| IGFBP-3 | 98.0 ± 13.16 | 111.25 ± 18.4 (0.2688) | 91.0 ± 6.38 (0.2968) | 123.67 ± 26.5 (0.2289) | 107.27 ± 21.2 (0.2842) |
| DHEA | 121.5 ± 39.91 | 89.25 ± 20.74 (0.13470) | 115.0 ± 33.64 (0.7889) | 115.67 ± 34.4 (0.8297) | 105.82 ± 29.6 (0.4229) |
| DHEAS | 83.2 ± 17.31 | 114.0 ± 13.14 (0.019) | 110.5 ± 14.18 (0.0355) | 120.0 ± 1.0 (0.0088) | 114.36 ± 11.3 (0.0116) |
| Total T4 | 95.6 ± 7.06 | 110.75 ± 12.5 (0.0893) | 107.75 ± 11.2 (0.1187) | 102.67 ± 17.8 (0.5685) | 107.46 ± 12.6 (0.0321) |
| Free T4 | 95.67 ± 17.1 | 93.25 ± 18.52 (0.8416) | 101.75 ± 14.1 (0.5581) | 113.0 ± 9.54 (0.0942) | 101.73 ± 15.7 (0.4897) |
| Total T3 | 95.67 ± 20.02 | 86.0 ± 6.58 (0.3117) | 91.75 ± 5.19 (0.664) | 99.0 ± 9.17 (0.7421) | 91.64 ± 8.18 (0.6537) |
| Androst.[1] | 9.83 ± 3.97 | 21.25 ± 14.66 (0.2176) | 22.75 ± 10.01 (0.0764) | 23.33 ± 4.73 (0.0175) | 22.36 ± 9.99 (0.0025) |
| Estradiol | 73.4 ± 19.6 | 179.25 ± 99.3 0.0121 | 108.25 ± 38.5 0.0170 | 113.0 ± 11.36 0.011 | 135.36 ± 68.2 0.016 |
| Prolactin | 103.83 ± 29.2 | 101.25 ± 24.2 (0.8833) | 111.25 ± 11.4 (0.5923) | 114.0 ± 33.29 (0.6787) | 108.36 ± 21.7 (0.7476) |
| LH | 69.83 ± 44.84 | 82.25 ± 57.41 (0.7291) | 118.75 ± 47.8 (0.153) | 101.33 ± 14.1 (0.5518) | 97.0 ± 47.24 (0.2743) |
| Cortisol | 113.2 ± 40.9 | 104.75 ± 42.5 (0.7725) | 96.25 ± 21.7 (0.4545) | 115.67 ± 11.2 (0.9039) | 104.64 ± 27.8 (0.6858) |
| CBG[2] | 97.4 ± 13.5 | 96.0 ± 7.83 (0.8517) | 101.0 ± 9.02 (0.6477) | 103.67 ± 13.9 (0.5641) | 99.91 ± 9.6 (0.7209) |
| Aldosterone | 45.33 ± 16.16 | 23.0 ± 6.58 (0.0189) | 37.75 ± 29.18 (0.6591) | 40.33 ± 11.24 (0.6091) | 33.09 ± 18.94 (0.1861) |
| SHBG[3] | 104.4 ± 20.45 | 88.75 ± 5.8 (0.1665) | 100.75 ± 14.9 (0.7658) | 127.33 ± 35.8 (0.39) | 103.64 ± 24.4 (0.9495) |
| EPO[4] | 163.0 ± 49.23 | 220.0 ± 51.02 (0.1267) | 202.0 ± 86.46 (0.4561) | 153.33 ± 10.5 (0.6618) | 195.27 ± 61.9 (0.2611) |

TABLE 2-continued

| ASSAY | Placebo | 0.3 mg/kg | 1.0 mg/kg | 3.0 mg/kg | Treatment* |
|---|---|---|---|---|---|
| Osteocalcin | 86.5 ± 51.74 | 159.75 ± 94.0 (0.2244) | 71.5 ± 24.91 (0.5587) | 125.67 ± 4.16 (0.1233) | 118.36 ± 66.5 (0.2939) |
| Bone AP[5] | 99.0 ± 16.33 | 106.5 ± 11.27 (0.4155) | 103.5 ± 8.1 (0.5807) | 100.0 ± 8.19 (0.9061) | 103.64 ± 8.86 (0.5403) |
| Procoll.[6] | 85.33 ± 24.28 | 105.75 ± 9.14 (0.1046) | 114.0 ± 14.9 (0.0496) | 113.0 ± 17.35 (0.1001) | 110.73 ± 13.0 (0.0508) |
| Active Renin | 138.5 ± 68.99 | 123.25 ± 77.5 (0.761) | 130.0 ± 37.5 (0.8081) | 109.33 ± 24.1 (0.3852) | 121.91 ± 49.1 (0.6165) |

Measurements obtained at the end of the study were expressed as a percentage of baseline levels in each patient prior to the first injection of IGF-I complex (rhIGF-I/IGFBP-3). An average (±SD) of these percentage values were then computed for each group. P values are shown in parentheses, and were calculated as a two-tailed, unpaired t-test computed versus placebo.
*values computed for a combined grouping of all three rhIGF-I/IGFBP-3 treatment groups
[1]Androstenedione
[2]Cortisol Binding Globulin
[3]Steroid Hormone Binding Globulin
[4]Erythropoietin
[5]Bone Alkaline Phosphatase
[6]Procollagen peptide The results clearly show that, in healthy volunteers, systemic administration of IGF-I complex results in significantly elevated levels of IGF-I, IGFBP-2, DHEAS, total T4, estradiol, androstenedione and procollagen peptide. Simultaneously, IGF-II levels are significantly lowered.

Significant elevation of DHEAS, estradiol and androstenedione levels (relative to placebo) occurs despite a reduction in aldosterone levels. DHEA, cortisol and CBG levels are not significantly changed in this study. Thus the change in circulating levels of adrenal steroids is quite specific and suggests a selective stimulation of cytochrome P-450c 17 lyase (versus hydroxylase) activity. This effect of IGF-I in vivo has not been previously demonstrated.

An increase in cytochrome b5 levels or activity might be responsible for the increase in P-450c17 lyase activity. After observing the effects of IGF-I complex on DHEAS levels, the 5'region of the cytochrome b5 gene was closely inspected. A portion of the 5' region of the cytochrome b5 gene was identified as containing a sequence that has similarity to an IGF-responsive element found in 450 scc, d1 crystalline and thyroglobulin genes. This potential IGF-responsive element in cytochrome b5 gene has not been previously described.

Total T4 were also elevated significantly by IGF-I complex administration in human subjects, while no significant changes were observed in free T4, total T3, TSH, or thyroglobulin levels. Such effects of IGF/IGFBP-3 complex in vivo have not been previously described.

The elevation of IGFBP-2 levels in response to IGF-I complex administration was also unknown. Also unknown is the effect of changing the ratio of circulating IGF-I to IGF-II, as accomplished in this study. IGFBP-3 levels were not significantly altered, however.

Circulating levels of procollagen peptide indicate the rate of collagen deposition in the tissues. Systemic administration of IGF-I complex elevates the level of this peptide significantly, suggesting a more anabolic state with respect to the formation of bone and other tissue. Other markers, including markers of bone turnover, were not significantly different between treatment and controls in this study.

Example 3

12 females, ages 55–70, were treated with rhIGF-I/IGFBP-3 complex (manufactured as described in Sommer et al., supra) by continuous subcutaneous infusion for seven days. Each dose group (placebo control, 0.5, 1.0 and 2.0 mg/kg/day rhIGF-I/IGFBP-3 complex) consisted of three subjects. rhIGF-I/IGFBP-3 was dissolved in 50 mM sodium acetate, 105 mM sodium chloride, pH 5.5 and diluted with normal (0.9%) saline. Blood samples were obtained before and following treatment.

Endocrine assays were performed as described in Example 2. Compared to placebo, statistically significant changes were observed in the levels of IGF-I, IGF-II, IGFBP-2, IGFBP-3, total T3 and TSH. Increases in total T4, DHEAS and procollagen peptide were also observed.

Example 4

Patients suffering from fibromyalgia are treated in a double-blind, placebo-controlled trial. Patients meeting the American College of Rheumatology criteria for fibromyalgia are randomly assigned into placebo and drug groups. Patients are assessed for the severity of their fibromyalgia prior to initiation of treatment, establishing a baseline. rhIGF-I/IGFBP-3 complex or placebo is administered by continuous subcutaneous infusion using a portable minipump. rhIGF-I/IGFBP-3 complex is administered for four or eight weeks.

Patients are assessed for the severity of their fibromyalgia symptoms at least once every two weeks following initiation of treatment. Assessments include patient reported pain and fatigue using a visual ranking scale, patient reported sleep quality, and other measures of fibromyalgia symptoms such as assessments of mood by the AIMS or Beck depression scales. rhIGF-I/IGFBP-3 complex reduces or alleviates the symptoms of fibromyalgia in drug-treated patients as compared to placebo-controlled patients.

Example 5

12 patients were treated with placebo or IGF-I/IGFBP-3 complex by continuous I.V. infusion for seven days (the same patients as in Example 3, above). Whole blood samples were collected prior to treatment (Day 1) and immediately following the end of the infusion (Day 8). RNA was extracted from whole blood samples as follows: Approximately 300 ul of blood was chipped out while frozen and thawed in 1 ml of denaturing solution from the Micro RNA Isolation Kit (Stratagene, cat#200344). The kit protocol was modified as follows: The cells were disrupted by passing the solution through a 22 gauge syringe needle 4 times. The phenol:chloroform extraction step was repeated twice. After precipitation with isopropyl alcohol, the pellet was resuspended in 100 μL RNAse-free water and 1 μL of DNAse was added and incubated at 37° C. for 15 minutes. Then another phenol:chloroform extraction and another precipitation. The final pellet was washed with 70% ETOH and dried. It was resuspended in 50 μL RNAse-free water. These RNAs were thawed and 20 μL was brought up to 33 μL with RNAse-free water for the cDNA reactions with the 'Ready-To-Go' T-Primed First-Strand Kit (Pharmacia, Cat.# 27-9263-01). For PCR, 2-5 μL of the cDNAs were used per reaction along with 1 μL each of the primers (b5 sense: 5'- . . . CCT GCA CCA CA AGG TGT ACG ATT . . . 3'; and b5 anti sense: 5' . . . TCC TCT GGC CAT GTA TAG GCG ATA C . . . 3') 10× PCR Buffer, 0.8 ul dNTPs, 0.5 μL Amplitaq (Perkin-Elmer Corp., Norwalk, Conn.) and brought up to 100 μL with dH20. These were run for 35–40 cycles on a thermocycler. The cycle profile used was: 95° C., 1 minute, 55° C., 30 minutes, 72° C. 30 minutes.

PCR products were analyzed by electrophoresis in agarose gels, followed by staining with ethidium bromide. PCR products were quantified by densitometric scanning of the stained gels. The results are shown in Table 3. Three of nine IGF-I complex-treated individuals, but none of three placebo-treated individuals, showed at least a 10-fold increase in b5 cytochrome PCR product from Day 8 samples as compared to Day 1 samples. For these three individuals, and the placebo controls, the experiment was performed at least twice for confirmation. All individuals (18 samples) amplified a control product using platelet factor 4 primers with comparable efficiency.

TABLE 3

|  | Day 1 (area) | Day 8 (area) | Ratio (D8/D1) |
|---|---|---|---|
| Placebo-treated controls: |  |  |  |
| Patient #008 | 4290 | 8661 | 2.02 |
| Patient #111 | 7981 | 10680 | 1.34 |
| Patient #202 | 6455 | 10003 | 1.55 |
| IGF-complex-treated: |  |  |  |
| Patient #005 | 354 | 13622 | 38.48 |
| Patient #006 | 1433 | 17531 | 12.23 |
| Patient #007 | 17069 | 14562 | 0.85 |
| Patient #201 | 42 | 3593 | 85.55 |
| Patient #203 | 8029 | 10844 | 1.35 |
| Patient #204 | 4966 | 7480 | 1.51 |

The patents, patent applications, and publications cited throughout the disclosure are incorporated herein by reference in their entirety.

The present invention has been detailed both by direct description and by example. Equivalents and modifications of the present invention will be apparent to those skilled in the art, and are encompassed within the scope of the invention.

I claim:

1. A method for treating or alleviating the the symptoms of aging or premature aging wherein said symptoms are associated with low circulating levels of sex steroids, comprising administering an effective amount of IGF to a subject in need of the treatment, wherein said administering results in an improvement in said symptoms.

2. The method of claim 1 wherein said IGF is IGF-I.

3. The method of claim 1 wherein said IGF is administered in combination with IGFBP-3.

* * * * *